US00PP25193P2

(12) United States Plant Patent
van Opstal

(10) Patent No.: US PP25,193 P2
(45) Date of Patent: Dec. 30, 2014

(54) *ABELIA* PLANT NAMED 'OPSTAL40'

(50) Latin Name: *Abelia×grandiflora*
Varietal Denomination: Opstal40

(71) Applicant: Ron van Opstal, Zundert (NL)

(72) Inventor: Ron van Opstal, Zundert (NL)

(73) Assignee: Ron van opstal holding B.V., Zundert (NL)

( * ) Notice: Subject to any disclaimer, the term of this patent is extended or adjusted under 35 U.S.C. 154(b) by 177 days.

(21) Appl. No.: 13/694,158

(22) Filed: Nov. 1, 2012

(51) Int. Cl.
*A01H 5/00* (2006.01)

(52) U.S. Cl.
USPC ..... Plt./226

(58) Field of Classification Search
CPC ..... A01H 5/02
USPC ..... Plt./226
See application file for complete search history.

(56) References Cited

PUBLICATIONS

Upov Pluto Plant Variety Database 20120603, retrieved on Jun. 9, 2014, retrieved from the Internet at <https://www3.wipo.int/pluto/user/en/index.jsp> for *Abelia* 'OPSTAL40', one page.*
Plantago—*Abelia grandiflora* opstal 40, retrieved on Jun. 9, 2014, retrieved from the Internet at <http://www.plantago.nl/plantindex/plant/BO/A/1/abelia-grandiflora-opstal-40/392039.html> one page.*

* cited by examiner

*Primary Examiner* — June Hwu
(74) *Attorney, Agent, or Firm* — Penny J. Aguirre

(57) ABSTRACT

A new cultivar of *Abelia×grandiflora* named 'Opstal40' that is characterized by its foliage that is irregularly variegated in spring and early summer with green centers and yellow margins and becoming suffused with orange and then red in mid summer through fall, its numerous blooms that open pinkish white in color and mature to white with red sepals, and its upright and broadly spreading plant habit.

2 Drawing Sheets

Botanical classification: *Abelia×grandiflora*.
Varietal denomination: 'Opstal40'.

BACKGROUND OF THE INVENTION

The present invention relates to a new and distinct cultivar of *Abelia×grandiflora* and will be referred to hereafter by its cultivar name, 'Opstal40'. 'Opstal40' represents a new *Abelia*, an herbaceous perennial grown for landscape use.

The inventor discovered the new cultivar, 'Opstal40', as a naturally occurring branch mutation of *Abelia×grandiflora* 'Abelops' (U.S. Plant Pat. No. 20,961) in August 2009 in a container in Zunder, The Netherlands.

Asexual reproduction of the new cultivar was first accomplished by the inventor by stem cuttings in Zundert, The Netherlands in October 2009. It has been determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Opstal40', as unique from all other selections and forms of *Abelia×grandiflora* known to the inventor.

1. 'Opstal40' exhibits foliage that is irregularly variegated in spring and early summer with green centers and yellow margins and becoming suffused with orange and then red in mid summer through fall.
2. 'Opstal40' exhibits numerous blooms that open pinkish white in color and mature to white with red sepals.

3. 'Opstal40' exhibits an upright and broadly spreading plant habit.

'Abelops', the parent plant of 'Opstal40', differs from 'Opstal40' in having foliage that turns reddish in color in autumn rather than summer, and in having flowers that remain pinkish white in color when mature. 'Opstal40' can also be most compared to the cultivar 'Kaleidoscope' (U.S. Plant Pat. No. 16,988) and 'Sunrise' (U.S. Plant Pat. No 9,698). 'Kaleidoscope' differs from 'Opstal40' in having variegated foliage with the leaves flushed with orange and red in autumn rather than summer, and in having pinkish white flowers that remain pinkish white when they are mature. 'Sunrise' differs from 'Opstal40' in having variegated foliage with green centers and golden yellow margins when young with the margins turning creamy white as the leaves mature.

BRIEF DESCRIPTION OF THE PHOTOGRAPHS

The plants and plant parts in the photographs depict a two-year old plant of 'Opstal40' as grown outdoors in an unheated greenhouse 17-cm container in Zundert, The Netherlands.

Figure 1:
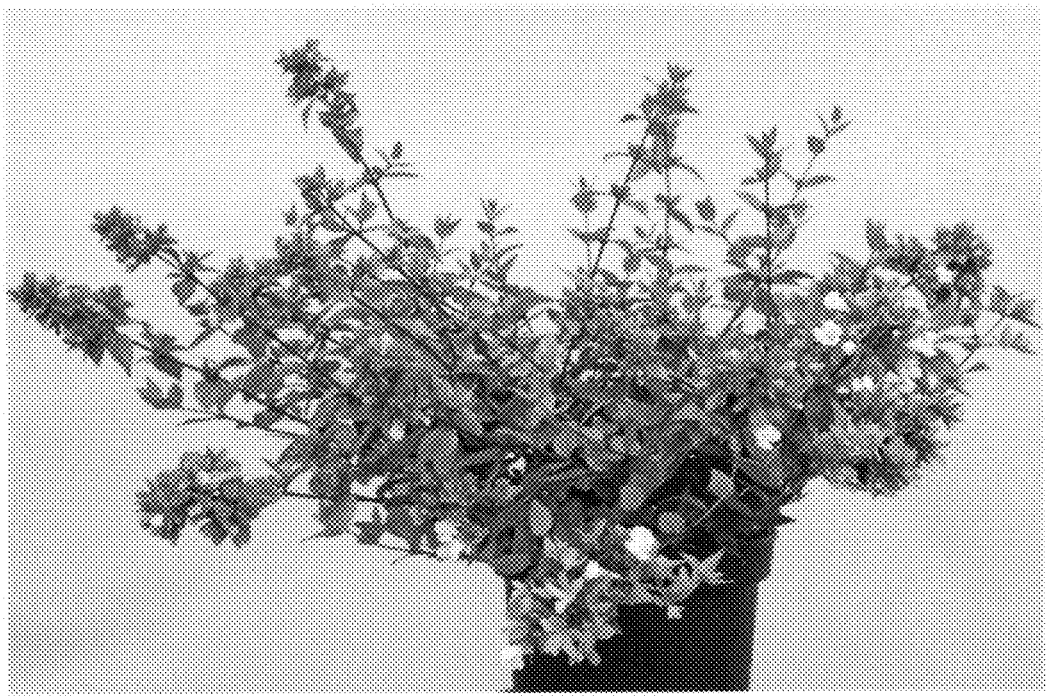

The photograph in FIG. 1 provides a side view of 'Opstal40' in bloom at the end of the summer.

Figure 2:
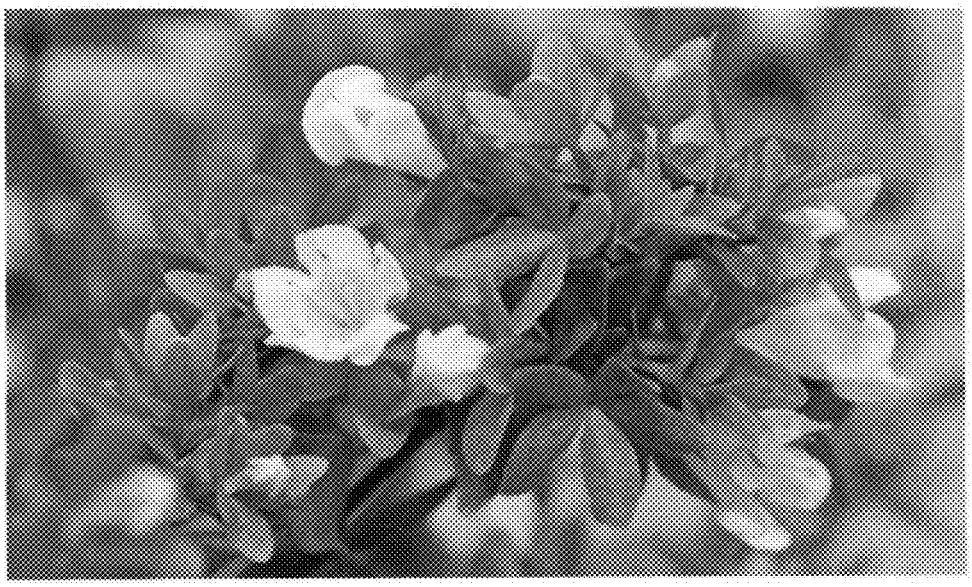

The photograph in FIG. 2 provides a close-up view of a flower of 'Opstal40'.

Figure 3:
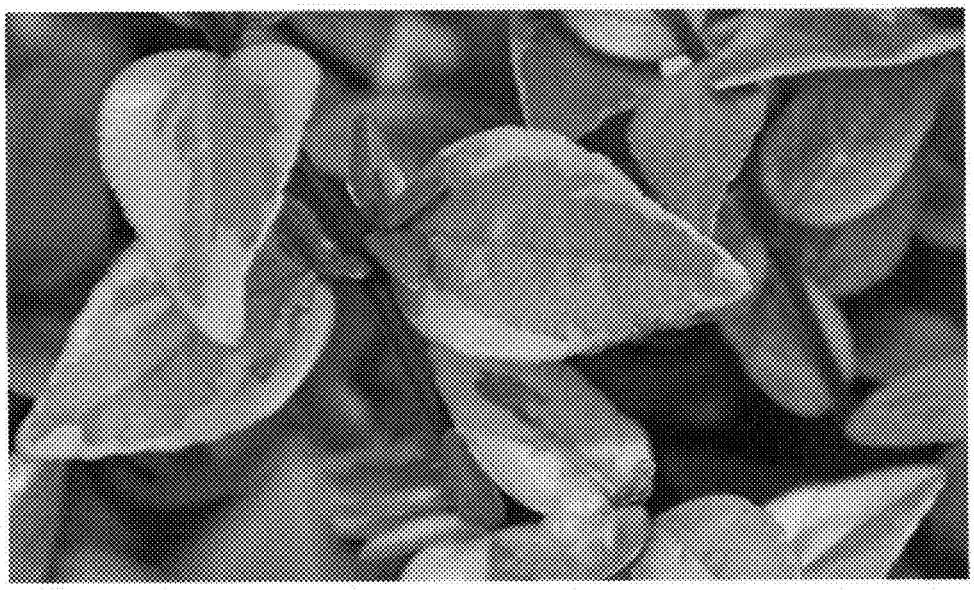

The photograph in FIG. 3 provides a close-up the foliage of 'Opstal40' in mid summer.

The colors in the photographs are as close as possible with the photographic and printing technology utilized and the color values cited in the detailed botanical description accurately describe the colors of the new *Abelia*. The colors in the photographs are as close as possible with the photographic and printing technology utilized. The color values cited in the detailed botanical description accurately describe the colors of the new *Abelia*.

DETAILED BOTANICAL DESCRIPTION

The following is a detailed description of two year-old plants of the new cultivar as grown in an unheated greenhouse in 17 cm containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Begins in mid July and continues for about 6 weeks.

*Plant type*.—Semi-evergeen shrub, observed to be deciduous in The Netherlands.

*Plant habit*.—Broadly spreading upright.

*Height and spread*.—Average of 28.6 cm in height and 49 cm in spread.

*Hardiness*.—Known to be hardy at least to U. S. D. A. Zone 7a.

*Diseases and pests*.—Not more susceptible to pests and diseases than other *Abelia* varieties.

*Root description*.—Fine, wiry, and freely branched.

*Propagation*.—Stem division.

*Growth rate*.—Moderate.

Stem description:

*Stem color*.—Young stems N186C and mature stems 187B.

*Stem size*.—Average of 19.9 cm in length and 2 mm in diameter.

*Stem quantity*.—Average of 35.

*Stem shape*.—Rounded.

*Stem surface*.—Moderately glossy with densely pubescent very short glandular hairs, average of 0.1 mm in length and to small to determine color.

*Stem aspect*.—Very strong.

*Branching habit*.—Free branching.

Foliage description:

*Leaf division*.—Single.

*Leaf attachment*.—Petiolate.

*Leaf arrangement*.—Opposite.

*Leaf number*.—Average of 18 (9 pairs).

*Leaf shape*.—Ovate.

*Leaf apex*.—Broad acute to obtuse.

*Leaf surface*.—Both surfaces thick and slightly leathery and smooth, upper surface very glossy and lower surface moderately glossy.

*Leaf base*.—Rounded to very short attenuate.

*Leaf venation*.—Pinnate, upper surface between 146A and 148A, lower surface 146C to 146D and densely pubescent near the base of the leaf blade, average length of hairs 0.4 mm and 157D in color.

*Leaf margin*.—Crenulate.

*Leaf color*.—Immature upper surface; 165A, irregular margins 166C, immature lower surface; 177B, irregular margins 166B, mature upper surface; ranging between 146A and 148A, irregular margins range from 151C and 151D to 168B and 168C with a thin margin of 34B, mature lower surface; 146D, irregular margins 153D with a thin margin of 34B, in mid summer through fall on both surfaces; coloration similar to mature leaves except they become suffused with 34A to 34B throughout the leaf.

*Internode*.—Average of 2.4 cm in length.

*Leaf size*.—Average of 2.6 cm in length and 1.7 cm in width.

*Petioles*.—Average of 3 mm in length and 1 mm in diameter, both surfaces 152D in color.

Flower description:

*Inflorescence type*.—Numerous single rotate shaped flowers arranged on pyramidal panicles.

*Inflorescence aspect*.—All directions.

*Inflorescence size*.—Average of 6.2 cm in height and 6.8 cm in width.

*Flower fragrance*.—Faint, sweet.

*Flower quantity*.—Average of 4.0 per inflorescence.

*Flower lastingness*.—Average of 5 days.

*Flower buds*.—Obovate in shape, slightly curved, average of 7 mm in diameter and 1.3 cm in length, color; 155A, tip slightly suffused with 182D, lower side tip 157D.

*Flower aspect*.—All directions.

*Flower shape*.—Campanulate.

*Flower size*.—About 2.6 cm in depth and 1.6 cm in diameter.

*Petals*.—Average of 5, campanulate, obovate in shape, margin is entire, apex is obtuse, upper (inner) surface is smooth and dull and covered with soft hairs 1 mm in length and NN155D to in color, under (outside) surface smooth and dull, color: upper (inner) surface when opening; NN155B and flushed lightly with 75C, lower (outer) surface when opening; NN155B flushed lightly with 75C to 75D, upper (inner) and lower (outer) surface when fully opened; NN155C to NN155D, average of 1.9 cm in length and 6 mm in width, 65% of the lower petals fused.

*Calyx*.—Rotate, average of 8 mm in length and 1.9 cm in diameter.

*Sepals*.—5, obovate to elliptic in shape, margin is entire, apex is obtuse, base is cuneate, both surfaces are smooth and dull, color: immature upper surface; 173A, tinged with 147A at the base, immature lower surface; 178C, mature upper and lower surface; 178C, suffused with 179B to 179C at the base, about 7 mm in width and 1.2 cm in length.

*Peduncles*.—Average of 4.1 cm in length and 1.5 mm in width, strong, color: upper surface; 187A, lower surface; 187B, glabrous surface, average angle of 0° (straight on top of lateral branch), secondary peduncles in an average angle of 50°.

*Pedicels*.—About 1 mm in length and 0.5 mm in width, strong, upper and lower surface 146A in color, glabrous surface, average angle: 0° (straight on top of peduncle), secondary pedicels in an average angle of 50°.

Reproductive organs:

*Gynoecium*.—1 pistil, about 1.3 cm in length, stigma 160C to 160D in color, club-shaped, style is about 1.2 cm in length and color is NN155B, base 149D in color, ovary is 174B to 174C, base 145B in color.

*Androcoecium*.—About 4 stamens, anthers are oblong in shape, basifixed, about 1.5 mm in length and N77B in color, filaments are about 1.3 cm in length and NN155D in color, pollen is moderate in quantity and 156D in color.

*Fruit and seed*.—No fruit or seed have been observed.

It is claimed:

1. A new and distinct cultivar of *Abelia* plant named 'Opstal40' as herein illustrated and described.

* * * * *